(12) United States Patent
Mailhe et al.

(10) Patent No.: US 10,810,767 B2
(45) Date of Patent: Oct. 20, 2020

(54) MACHINE-LEARNED NETWORK FOR FOURIER TRANSFORM IN RECONSTRUCTION FOR MEDICAL IMAGING

(71) Applicant: Siemens Healthcare GmbH, Erlangen (DE)

(72) Inventors: Boris Mailhe, Plainsboro, NJ (US); Simon Arberet, Princeton, NJ (US); Florent Billy Romaric Gbelidji, Monmouth Junction, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 210 days.

(21) Appl. No.: 16/150,304

(22) Filed: Oct. 3, 2018

(65) Prior Publication Data
US 2019/0378311 A1    Dec. 12, 2019

Related U.S. Application Data

(60) Provisional application No. 62/683,790, filed on Jun. 12, 2018.

(51) Int. Cl.
*G06T 11/00*        (2006.01)
*G06N 3/04*         (2006.01)
(Continued)

(52) U.S. Cl.
CPC .......... *G06T 11/006* (2013.01); *G06F 17/142* (2013.01); *G06N 3/0454* (2013.01); *G06N 3/08* (2013.01); *G16H 30/40* (2018.01)

(58) Field of Classification Search
None
See application file for complete search history.

(56) References Cited

U.S. PATENT DOCUMENTS

2018/0203081 A1* 7/2018 Cohen .................... G01R 33/50
2018/0285695 A1* 10/2018 Guo ..................... G06T 7/0012
(Continued)

FOREIGN PATENT DOCUMENTS

WO    WO-2017113205 A1 *  7/2017 ............... G06N 3/08

OTHER PUBLICATIONS

S. Tang, F. Jan, H. Cheng, C. Lin and G. Wu, "Multimode Memory-Based FFT Processor for Wireless Display FD-OCT Medical Systems," in IEEE Transactions on Circuits and Systems I: Regular Papers, vol. 61, No. 12, pp. 3394-3406, Dec. 2014, doi: 10.1109/TCSI.2014.2327315. (Year: 2014).*
(Continued)

*Primary Examiner* — Kim Y Vu
*Assistant Examiner* — Nathan J Bloom (57) ABSTRACT

For low-complexity to learned reconstruction and/or learned Fourier transform-based operators for reconstruction, a neural network is used for the transform operators. The network architecture is modeled on the Cooley-Tukey fast Fourier transform (FFT) approach. By splitting input data before recursive calls in the network architecture, the network may be trained to perform the transform with similar complexity as FFT. The learned operators may be used in a trained network for reconstruction, such as with a learned iterative framework and image regularizer.

19 Claims, 4 Drawing Sheets

(51) Int. Cl.
*G06F 17/14* (2006.01)
*G16H 30/40* (2018.01)
*G06N 3/08* (2006.01)

(56) References Cited

U.S. PATENT DOCUMENTS

| | | | |
|---|---|---|---|
| 2018/0373677 A1* | 12/2018 | Jaber | G06F 7/78 |
| 2019/0172230 A1* | 6/2019 | Mailhe | G06T 5/002 |
| 2019/0257905 A1* | 8/2019 | Cheng | G01R 33/5611 |
| 2019/0266761 A1* | 8/2019 | Malkiel | G06T 11/008 |
| 2019/0325621 A1* | 10/2019 | Wang | A61B 6/037 |

OTHER PUBLICATIONS

Mohammadnia, Mohammad Reza. "Precision and reliability of application specific designs on FPGA." PhD diss., Applied Sciences: School of Engineering Science, 2017. (Year: 2017).*

M. R. Mohammadnia and L. Shannon, "Minimizing the error: A study of the implementation of an Integer Split-Radix FFT on an FPGA for medical imaging," 2012 International Conference on Field-Programmable Technology, Seoul, 2012, pp. 360-367, doi: 10.1109/FPT.2012.6412161. (Year: 2012).*

Hammernik, Kerstin, et al. "Learning a variational network for reconstruction of accelerated MRI data." Magnetic Resonance in Medicine 79:3055-3071 (2018).

Mardani, Morteza, et al. "Deep generative adversarial networks for compressed sensing automates MRI." arXiv preprint arXiv:1706.00051 (2017).

Zhu, Bo, et al. "Image reconstruction by domain-transform manifold learning." Nature 555.7697 (2018).

U.S. Appl. No. 15/471,079, filed Mar. 28, 2017.
U.S. Appl. No. 15/832,967, filed Dec. 6, 2017.

* cited by examiner

MACHINE-LEARNED NETWORK FOR FOURIER TRANSFORM IN RECONSTRUCTION FOR MEDICAL IMAGING

RELATED APPLICATION

The present patent document claims the benefit of the filing date under 35 U.S.C. § 119(e) of Provisional U.S. Patent Application Ser. No. 62/683,790, filed Jun. 12, 2018, which is hereby incorporated by reference.

BACKGROUND

The present embodiments relate to Fourier transform in reconstruction. Most medical scanners (e.g. ultrasound, computed tomography (CT), x-ray, magnetic resonance (MR), positron emission tomography (PET), or single photon emission computed tomography (SPECT)) acquire data in a tomographic domain different from the spatial pixel maps (i.e., Cartesian display format) showed to the user. To transform the scan data in the measurement domain to the image domain, image reconstruction is performed. More advanced iterative reconstruction methods may be used to model non-Gaussian noise (e.g. Poisson in CT) missing data (e.g. MR compressed sensing) or other types of artifacts in the data (e.g. metal artifact correction in CT). Iterative reconstruction uses multiple back and forth transforms between the measurement (raw data) and image domains. The iterative reconstruction may be computationally expensive, result in less than optimal quality, and/or time consuming.

Deep learning may be applied to image reconstruction to reduce computation, improve image quality, and/or improve reconstruction time. For reconstruction, convolutional neural networks (CNN) may learn image regularizers in the image domain but do not have the capacity to learn tomographic reconstruction operators between raw data and images. Hybrid approaches only learn the iterative framework (i.e., convergence parameters) and the image regularizer while still using the same user-defined reconstruction operator as in non-trained iterative image reconstruction for data consistency. The user-defined reconstruction operators for forward and adjoint measurements make assumptions about the input data (e.g. replacing missing measurements by zeros) that may be suboptimal. The reconstruction operators may be modeled using a fully connected network to learn an optimal operator. The storage and computation complexities of fully connected networks are quadratic in the number of pixels of the image, which precludes their use for high-resolution or three-dimensional (3D) imaging applications. Reconstruction of two-dimensional (2D) images greater than 128×128 pixels or 3D volumes, common for medical imaging, may require prohibitively large fully connected networks.

SUMMARY

Systems, methods, and instructions on computer readable media are provided for low-complexity to learned reconstruction and/or learned Fourier transform-based operators for reconstruction. A neural network is used for the transform operators. The network architecture is modeled on the Cooley-Tukey fast Fourier transform (FFT) approach. By splitting input data before recursive calls in the network architecture, the network may be trained to perform the transform with similar complexity as FFT. The learned operators may be used in a trained network for reconstruction, such as with a learned iterative framework and image regularizer.

In a first aspect, a method is provided for converting data between scan space and image domain in an imaging system. The imaging system scans an object. The scan results in input data. A transform of the input data is performed based on application of the input data to a machine-learned neural network. The machine-learned neural network includes an architecture of a sequence of a convolutional splitting layer, parallel recursive deep networks, a diagonal linear layer, and a convolutional butterfly layer. Image domain data is generated from an output of the machine-learned neural network. An image from the image domain data is displayed.

In a second aspect, a system is provided for reconstruction in medical imaging. A medical scanner is configured to scan a patient, the scan providing scan data. A reconstruction processor is configured to reconstruct an image from the scan data and to reconstruct with a machine-learned neural network containing blocks having a radix fast Fourier transform architecture. A display is configured to display the image as reconstructed from the scan data.

In a third aspect, a method is provided for Fourier transform-based reconstruction in a medical imaging system. The medical imaging system scans a patient, resulting in scan data representing the patient. An image of the patient is reconstructed from the scan data. The reconstruction is based on a model of the medical imaging system. The model includes a transformation implemented by a trained neural network having a convolution layer to split an input prior to a layer for recursive calls. The image of the patient is displayed.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

A machine-learned fast transform network is provided for artificial intelligence (AI)-based processing of raw scanner data. This transform network provides a low-complexity approach to fully-learned reconstruction and/or transform operators. A fast, scalable, transform network architecture based on the Cooley-Tukey FFT is used for the transform. The deep network architecture is based on the radix FFT to learn optimal reconstruction operators which remain in the same O(n log n) complexity class as the FFT, with n the number of pixels in the target image. The radix FFT and the corresponding architecture includes four layers: a layer to split the inputs into coefficients of even and odd indices, a layer for recursive application of an FFT on both half-sized signals, a layer for a pointwise multiplication with unit-norm twiddle factors, and a layer to reconstruct the whole-length output as the sum and difference of the half-length FFTs. This transform architecture may be used in a fully-learned iterative reconstruction with a U-net or other image regularization.

The network architecture has the capacity to learn tomographic operators while preserving the computational complexity of the FFT. Operators that perform more useful computations than the typical adjoints or pseudo-inverse are learned towards the goal of final image reconstruction. The learning process may allow the network to incorporate some of the image model into the reconstruction operator itself. As compared to a fully connected network, the radix FFT network architecture is more computationally efficient and uses less storage. Since the fast network has O(n log n) free parameters compared to $O(n^2)$ in a fully connected network, the neural network may be easier to train and less prone to overfitting.

Figure 1:
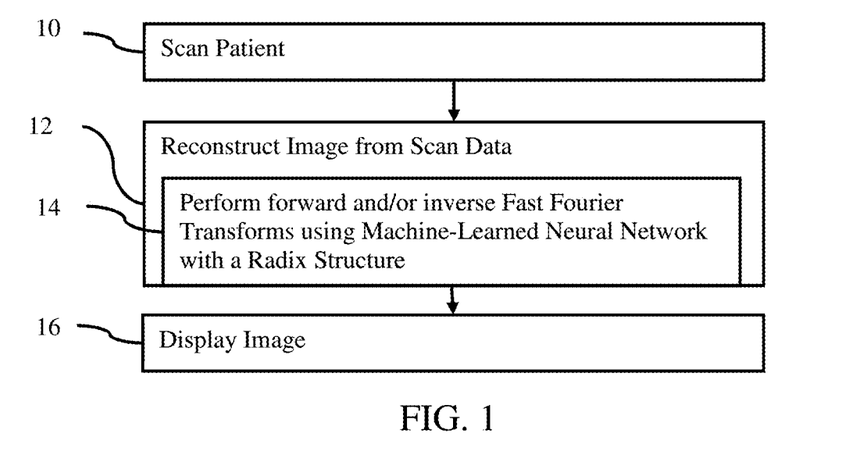
FIG. 1 illustrates one embodiment of flow chart of a method for transform-based reconstruction in an imaging system.

FIG. 1 shows one embodiment of a flow chart of a method for Fourier transform-based reconstruction in a medical imaging system. The Fourier transform is implemented with a machine-learned neural network. The architecture of the neural network includes a convolutional layer for splitting prior to layers for recursive calls. The architecture is based on or emulates the Cooley-Tukey approach to FFT.

Figure 6:
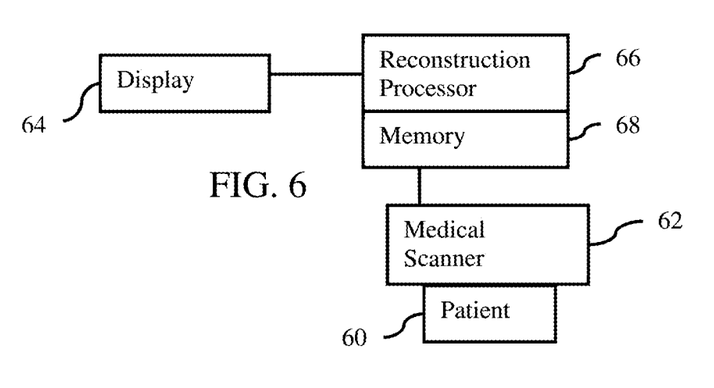
FIG. 6 is a block diagram of one embodiment of a system for transformation and/or reconstruction in medical imaging.

The system of FIG. 6 performs the acts of the method of FIG. 1. For example, the medical scanner 62 performs act 10, and the reconstruction processor 66 performs acts 12 and 14. The reconstruction processor 66, using the display 64, performs act 16. Other devices or hardware may be perform any of the acts.

The method is implemented by and/or using a medical imaging system. More than acquiring and outputting data, the medical imaging system is modeled as part of reconstruction. The transform implemented by the machine-trained neural network is at least part of a model of the physics of the medical imaging system. For example, the medical imaging system is a MR scanner or imaging system. The physics of the MR scanner results in measurements as k-space data, which is to be transformed to an image domain. The machine-trained neural network implements the transformation. For iterative reconstruction, one or more machine-trained neural networks implement the forward and backward (adjoint) measurement operators or transformations.

Other transforms may be implemented. The examples below are for MR reconstruction, but Fourier or other transforms for reconstruction in other types of medical imaging may be used, such as CT, PET, SPECT, or ultrasound. Other types of imaging systems may be used, such as a depth camera.

The method is provided in the order shown (e.g., top to bottom or numerical), but other orders may be provided. For example, act 14 is performed prior to the reconstruction or as part of the reconstruction of act 12.

Additional, different or fewer acts may be provided. For example, act 16 is not provided. As another example, acts for training the network and/or configuring the scanner are provided.

In act 10, the medical imaging system scans a patient. For example, a MR scanner scans the patient, resulting in MR scan data. The resulting scan data is received from or by the MR scanner. The receipt is by scanning the patient using a scan sequence. The type and/or protocol of the sequence define settings for various parameters for scanning and/or generating an image from the scan. Alternatively, the receipt of the MR scan data is by receiving from a network interface. In other embodiments, receipt is by loading from memory.

The MR scan data is k-space data measured by the coils of the MR scanner. The MR scan data is from a single scan or scan sequence. The scan is a 2D or 3D scan. For example, MR scan data is acquired as k-space data responsive to or representing a planar region of the patient or a volume of the patient (e.g., multiple stacked planes or slices). The response from two or three spatial dimensions is detected by scanning, providing scan data in the measurement domain.

In act 12, a reconstruction processor reconstructs an image of the patient from the scan data. The reconstruction is from the measurement domain (e.g., k-space data) to the image or object domain. Alternatively or additionally, the reconstruction includes transformation from the object domain to the measurement domain. The reconstructed object may be pixels, voxels, or scalar values on a gird (e.g., Cartesian coordinate). The reconstructed object may be a 2D or 3D object. The reconstructed image may be 2D or 3D scalars where further mapping and/or rendering generates the image for the 2D display (e.g., RGB pixel values).

The reconstruction is based on a model of the medical imaging system. In the MR scanner example, the model of the imaging system includes a Fourier transformation for transforming the k-space measurements to the image domain. The Fourier transformation models the physics of the MR measurements relative to the patient. The reconstruction may include a regularizer or prior. The regularizer is an expectation of the object in the image domain. The reconstruction includes fitting the patient-specific image domain data to the regularizer.

The model is used for a single conversion from the measurement domain to the image domain. In an iterative approach, the model may be used for forward and/or adjoint (e.g., backward or inverse) transformation from the measurement domain to the image domain and/or image to measurement in an iterative reconstruction. The transformation is repeated between the domains to optimize the fit of the measurements to the object. The repetitions occur until an error or other metric reaches a threshold or for a given number of times.

In one embodiment, a machine-learned neural network generates the image domain data from the measurement domain data. For example, the machine-learned reconstruction network is trained with gradient descent and regularization. In one embodiment, a reconstruction network is trained to reconstruct 2D MR images from under-sampled k-space data. The network structure mimics 10 iterations of a proximal gradient algorithm. At each iteration, the network performs a decent followed by a regularization step, as described by:

$$X_n \leftarrow R_n(X_{n-1} + \alpha_n F_n^h(Y - \Pi F_n X_{n-1}))$$

where $X_n$ is the image reconstructed at $n^{th}$ iteration, Y is the under-sampled k-space measurements, $\Pi$ is the fixed under-sampling operator, $F_n$ and $F_n^h$ are the forward and adjoint measurement operators, $\alpha_n$ is the trainable gradient step size, and $R_n$ is the regularizer. Regularizer networks may be implemented using residual U-nets with 2 scales, 8 channels in the hidden layers, and a depth of 1 at each scale. A U-net, image-to-image, or generative adversarial network may be trained to reconstruct. Other network architectures may be used. For example, any of the machine-learned reconstruction networks disclosed in U.S. Published patent application Nos. (application Ser. No. 15/832,967, filed Dec. 6, 2017, or Ser. No. 15/471,079, filed Mar. 28, 2017) may be used. As another example, a hybrid reconstruction is used.

Rather than relying on user-defined or hand coded transformation, the reconstruction uses a machine-learned network to transform. The forward and/or adjoint measurement operators are implemented by a machine-learned neural network in the reconstruction. Rather than using a fully connected network, the machine-learned network for transformation has an architecture to preserve the complexity of FFT.

The learned FFT network is integrated into a larger reconstruction network, such as part of the U-net. The learned FFT network may be implemented separately from the reconstruction network, such as being called by the reconstruction network. The machine-learned neural network for transformation (i.e., for the measurement operator) may be included in a machine-learned network for reconstruction. In one embodiment, the fast operator architecture is integrated as a plug-in replacement for measurement operators in an iterative reconstruction network. The machine-learned neural network for transformation is integrated as a direct (i.e. non-iterative) reconstruction followed by a convolutional neural network (CNN) for regularization or integrated as the branches connecting the input measurements to intermediate features in a deep learning architecture using skip connections such as DenseNet. Alternatively, the reconstruction may be hand-coded while using the machine-learned neural network for the transformation.

For the special case of MR compressed sensing when reconstruction is performed with missing data, the machine-learned neural network for the operator or transformation may also accept a sampling mask along with the measurements (k-space scan data). The sampling mask indicates locations with missing data. Learning to transform with input, in part, including the sampling mask allows the machine-learned neural network for the operator to be a single network trained to reconstruct images acquired with multiple sampling patterns.

The model of the medical imaging system used in reconstruction includes the trained neural network for transformation. For training, a machine learning network architecture is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning. Any part of the network architecture is defined.

The network arrangement is a neural network for deep learning. Deep architectures include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through back-propagation. DBN, on the other hand, employs the layer-wise unsupervised training (e.g., pre-training) followed by the discriminative refinement with back-propagation if necessary. Other networks and corresponding layers may be used, such as user defined layers to implement a specific function.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. For recursive calls, the layer may reduce scale repetitively with an architecture applied for each scale until a scale of one or two is reached. The nodes of each layer or unit may connect with all or only a sub-set of nodes of a previous and/or subsequent layer or unit. Skip connections may be used, such as a layer outputting to the sequentially next layer as well as other layers.

Rather than pre-programming the features and trying to relate the features to attributes, the deep architecture is defined to learn the features based on an input scan data (e.g., k-space data) with or without pre-processing. Various units or layers may be used, such as convolutional, pooling (e.g., max-pooling), deconvolutional, fully connected, user defined layers (e.g., diagonal operators), or other types of layers. Within a unit or layer, any number of nodes is provided. For example, 100 nodes are provided. Later or subsequent units may have more, fewer, or the same number of nodes.

The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network.

For training, the network uses samples of input scan data and corresponding transform image object data and/or reconstructed images as ground truth. The deep machine learning learns the convolution kernels, weights, connections, and/or other variables (parameters) to perform the transformation and/or reconstruction. Once trained, the machine-learned neural network for transformation performs, in act 14, the transformation (e.g., FFT) given input k-space data. The scan data is applied to the machine-learned neural network for transformation.

The neural network for transformation has an architecture to preserve complexity. The architecture has a convolution layer to split an input. The convolution has a stride of R and R output channels, where R is the radix size. The convolution layer feeds its R channels of output to a layer for R recursive calls. This splitting arrangement models the Cooley-Tukey FFT algorithm structure. For example, the radix-2 Cooley-Tukey FFT structure includes even and odd splitting of data and recursive calls based on the even and odd split.

Figure 2:
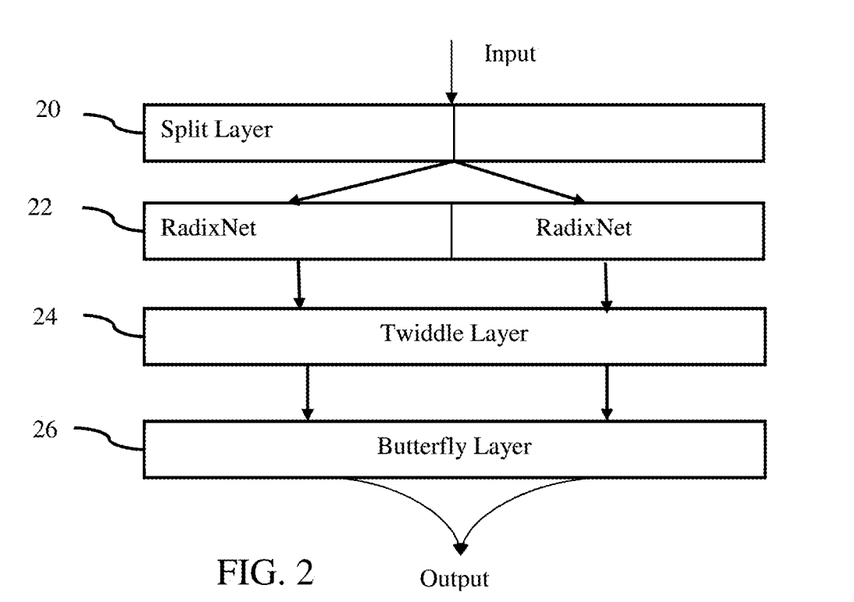
FIG. 2 illustrates an example neural network architecture for a measurement operator for transformation.

FIG. 2 shows an example architecture for the operators $F_n^h$. The architecture (RadixNet) models a structure of a radix FFT, which is a recursive complex-valued transform network composed of 4 blocks. The structure of the Cooley-Tukey FFT algorithm provides a sequence of layers including a strided convolutional splitting layer 20, parallel recursive deep networks 22, a diagonal linear layer (e.g., twiddle layer 24), and a convolutional butterfly layer 26. Parallel indicates a layer operating on different input channels and/or output channels. The layers are shown in sequence in FIG. 2. The architecture of the machine-learned network is structured as a radix FFT. A convolution layer or layers model the split (split layer 20) and another subsequent layer or layers 22 model the recursive calls. Additional, different, or fewer layers may be provided. Each block or layer is a single layer or may be deeper (e.g., the split layer 20 or butterfly layer 26 being formed from two or more neural network layers). Linear or nonlinear layers may be used.

The architecture is used to train the neural network to transform, such as a FFT. To enable training while maintaining the low complexity of the FFT, the network architecture (RadixNet) is used. While the architecture is based on the Cooley-Tukey FFT, one or more functions of the Cooley-Tukey FFT may not be enforced. For example, the split layer 20 and butterfly layer 26 are formed by convolution layers without requiring an actual split by even and odd and without requiring the specific butterfly function.

The split layer 20 is modeled after the even and odd split of Cooley-Tukey FFT. This even and odd split is represented by:

$$X = \begin{pmatrix} x_0 & x_1 \\ \vdots & \vdots \\ x_{2i} & x_{2i+1} \\ \vdots & \vdots \\ x_{n-2} & x_{n-1} \end{pmatrix}.$$

The split layer 20 may include a convolution layer with multiple output channels (two parallel convolution layers in terms of the output). The same input is provided to the layer. This split arrangement where two output channels are provided models the split of data between even and odd or other numbers of coefficients, frequencies, bins, or values. The split of data may not be enforced. Instead, the convolution kernels are learned with this split architecture. Even and odd output channels of the splitting layer 20 are provided in the architecture without requiring the layer to perform an even and odd split. The convolution layers of the split layer 20 are trained as part of end-to-end training. Alternatively, the convolution layers of the split layer 20 are trained to split even and odd data. In either approach, two different output channels are provided to the recursive layer 22.

Since the split is shift invariant, the split layer 20 may be performed by a CNN. A single layer of CNN may be used. In other embodiments, the CNN has a greater depth (e.g., multiple convolutional layers). Since the complexity is to be maintained, the split layer 20 is to provide a single output channel (e.g., 2 parallel split layers 20 providing 2 output channels or one split layer 20 providing 2 output channels).

Where multiple convolution layers are used for a split layer 20, different arrangements may be provided. For example, three convolution layers are used with a leaky ReLU following each layer. The first layer (e.g., with kernel size 3 and stride of 1) has 1 input channel with p output channels. The second layer (e.g., with kernel size 3 and stride of 1) hasp input channels with q output channels. The third layer (e.g., with kernel size 3 and stride of 2) has q input channels and 2 output channels for the split. The depth and width of the CNN are design parameters, but the number of output channels of the split network is equal to the overall stride of the whole split network (e.g., 2) to preserve the O(n log n) complexity.

The RadixNet layers are the recursive deep networks. The same architecture at reducing scale is provided for the recursive calls. The architecture of FIG. 2 is based on radix FFT, so the layer 22 recursively calls the same architecture. Since the RadixNet layer 22 is separate for the split, each operates on ½ the data in the Cooley-Tukey FFT. Each recursive call further reduces the scale. The entire architecture of FIG. 2 is called again, forming nested radix FFT networks at iteratively reducing scales. Recursive calls to another RadixNet on each decimated channel are used to implement the FFT. FFT is recursively applied on both half-sized signals or both signals output by the split layer 20. The recursive FFT call may be implemented by an actual recursive call (i.e., network weights are shared across scales) or by a recursive constructor that instantiates a new radix network at each scale (i.e. weights are not shared). FIG. 2 represents this second approach. The number of parameters O for all the network and input of size N of the scan data results in the number of recursions being: $r=\log_2(N)$. In alternative embodiments, the recursive calls are repetitions through the split layer 20 by the output of the split layer 20.

The recursion stops when the input size reaches a given threshold, and the output of the final scale is computed by computing the analytical Fourier transform using any algorithm, e.g. a non-trainable FFT. As a special case, the threshold can be set to 1. In that case, the output of the final scale is equal to the input once the transform is fully trained.

The twiddle layer 24 is formed from a diagonal operation layer. For each output channel (e.g., 2 for 1D), a twiddle layer 24 is provided. Each parallel twiddle layer receives a respective output from the recursive layer 22. Alternatively, a single block or layer forms the twiddle layer 24.

The twiddle layer 24 is defined to be a diagonal operator, i.e. a pointwise multiplication of every input coefficient with a trained weight. The twiddle layer 24 is a neural network layer defined to learn weights in diagonal linear operations.

The twiddle layer 24 performs a pointwise multiplication with unit-norm twiddle factors. The twiddle factor multiplication is a diagonal operator applied after recursive FFT. Using the Fourier convolution theorem, this is equivalent to a convolution applied before the recursive FFT. In the case of the FFT, the image-domain convolution kernel equivalent to the twiddle factor has a large support, which may make it hard to approximate with a CNN. The twiddle factors may be implemented in the trained network: (a) before the FFT call, with a CNN, (b) before the FFT call, with a deep Recurrent Neural Network (RNN where the linear layers are Infinite Impulse Response (IIR) filters suitable to represent the FFT twiddle factors), or (c) after the FFT with the diagonal linear operator.

In one embodiments, the twiddle factors are not constrained to have magnitude 1, and the trainable parameters of the network are the weights themselves. In other embodiments, unit-norm twiddle factors are represented as complex exponentials $\omega_n = e^{\varphi 1_e}$, and the trainable parameters of the network are the phases: $\varphi 1_e$ and $\varphi 1_o$ for the even, e, and odd, o, channels. The weights or parameters of the weights in the layer with the defined or enforced linear diagonal operation are learned in training.

The butterfly layer 26 is a convolution layer. In the Cooley-Tukey FFT, the butterfly performs a sum and difference operation. The sum and difference operation is represented by:

$$\begin{pmatrix} 1 & 1 \\ 1 & -1 \end{pmatrix} \begin{pmatrix} y_i^{[0]} \\ \omega_n^i y_i^{[1]} \end{pmatrix} = \begin{pmatrix} y_i^{[0]} + \omega_n^i y_i^{[1]} \\ y_i^{[0]} \omega_n^i y_i^{[1]} \end{pmatrix}.$$

where the 1 and −1 matrix represents the sum and difference operation with the twiddle weighted output of the twiddle layer 24.

For the architecture, the sum and difference operation may not be enforced. Instead, the convolution layer is part of the architecture, and the training learns the convolution to result in the desired output. The butterfly layer 26 provides a final convolution for the output. Separate convolution blocks or layers are provided for the two channels. Alternatively, the two channels are input to the single butterfly layer 26 or block, which outputs the output channel. The butterfly layer 26 reconstructs the whole-length transformed output as the sum and difference of the half-length FFTs. Since the reconstruction is shift-invariant, the convolution layer (e.g., CNN) may be used.

In one embodiment, the butterfly layer is deeper by being formed from a plurality of convolution layers. A CNN is provided. For example, the CNN includes a sequence of 3×3 convolution, CReLU, 3×3 convolution, CReLU, 3×3 convolution, CReLU and 3×3 convolution with the first layer forming M channels from one input and the last layer forming 1 output from M input channels. A feedforward from the first to the third 3×3 convolution may be used. The same arrangement of layers may be repeated any number of times. Other layer arrangements and/or kernel sizes may be used.

The number of output channels prior to reconstruction is equal to the stride of the split layer 20 or number of parallel convolution split layers 20. The data split is by two for even and odd in radix-2 FFT. While the trained network may not enforce the same even/odd split, the number of channels is enforced by the architecture. In the example of FIG. 2, there are two channels output by the split layer 20. The reconstruction for the butterfly layer 26 receives the two channels of data to reconstruction the output.

For two-dimensional reconstruction, a separable implementation may be provided. The operator is implemented as a succession of 1D operators along each dimension. This is represented by:

$$F(u, v) = \frac{1}{M} \sum_{m=0}^{M-1} \left[ \frac{1}{N} \sum_{n=0}^{N-1} \exp\left(\frac{-2\pi i n v}{N}\right) f(m, n) \right] \exp\left(\frac{-2\pi i m u}{M}\right),$$

$$u = 0, 1, \ldots, M-1, \quad v = 0, 1, \ldots, N-1.$$

Alternatively, the convolution split layer 20 is two-dimensional. In case of a radix-2 transform, the number of output channels increases to four—data for each dimension being split in two. For example, four outputs for the convolution layer or blocks are provided for the split layer 20. To extend the operators to multiple dimensions, a multidimensional radix that splits the data along each dimension is provided. The convolution layers are 2D or 3D (i.e., the inner CNN of the RadixNet (e.g., split layer 20 and butterfly layer 26) are multi-dimensional. 2D FFT is performed without stacking 1D FFT networks. The architecture mimics the Vector Radix 2×2 algorithm, which first decomposes the DFT into 2×2 partial sums as follows:

$$X(k, l) = \sum_{c=0}^{N-1} \sum_{r=0}^{N-1} x(c, r) W_N^{ck+rl} =$$

$$\sum_{i=0}^{1} \sum_{j=0}^{1} \sum_{m=0}^{N/2-1} \sum_{n=0}^{N/2-1} x(2m+i, 2n+j) W_N^{(2m+i)k+(2n+j)l} =$$

$$\sum_{i=0}^{1} \sum_{j=0}^{1} W_N^{ik+jl} \cdot \left\{ \sum_{m=0}^{N/2-1} \sum_{n=0}^{N/2-1} x(2m+i, 2n+j) W_{N/2}^{mk+nl} \right\} =$$

$$\sum_{i=0}^{1} \sum_{j=0}^{1} W_N^{ik+jl} S_{ij}(k, l).$$

Each partial sum denoted by $S_{i,j}(k,l)$ is a 2D DFT of size N/2×N/2, as represented by:

$$S_{ij}(k, l) = S_{ij}\left(k + \frac{N}{2}, l\right) = S_{ij}\left(k, l + \frac{N}{2}\right) = S_{ij}\left(k + \frac{N}{2}, l + \frac{N}{2}\right).$$

$$\begin{bmatrix} X(k, l) \\ X\left(k + \frac{N}{2}, l\right) \\ X\left(k, l + \frac{N}{2}\right) \\ X\left(k + \frac{N}{2}, l + \frac{N}{2}\right) \end{bmatrix} = \begin{bmatrix} 1 & 1 & 1 & 1 \\ 1 & -1 & 1 & -1 \\ 1 & 1 & -1 & -1 \\ 1 & -1 & -1 & 1 \end{bmatrix} \begin{bmatrix} S_{00}(k, l) \\ W_N^k S_{10}(k, l) \\ W_N^l S_{01}(k, l) \\ W_N^{k+l} S_{11}(k, l) \end{bmatrix}.$$

The input scan data is split into four channels with four recursive calls.

Figure 3:
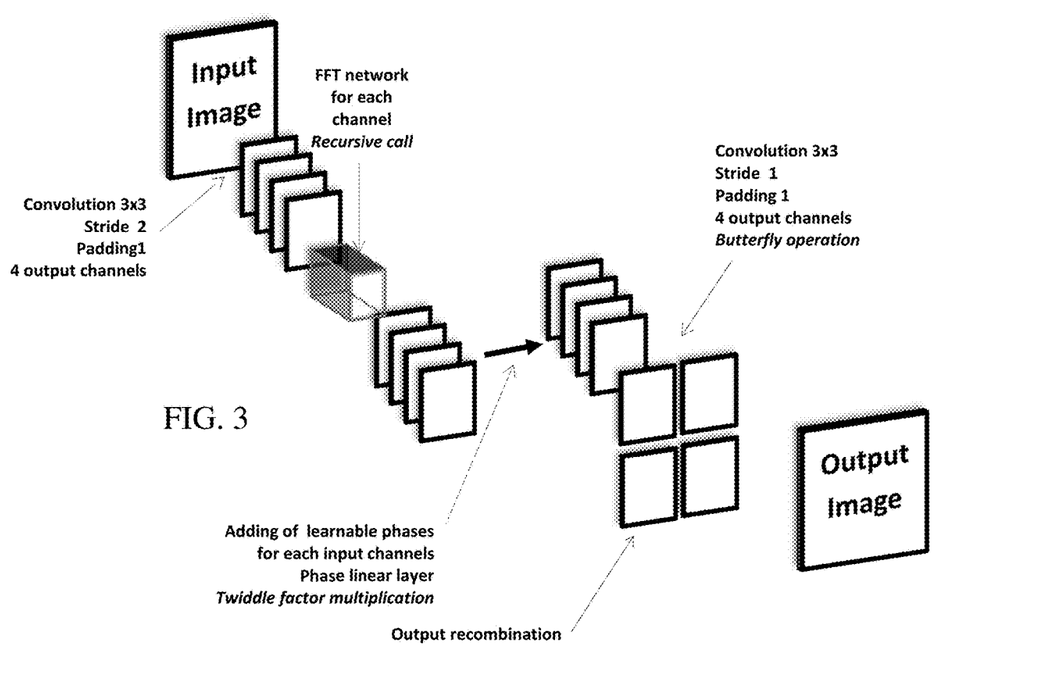
FIG. 3 illustrates another example neural network architecture for a measurement operator for transformation.

FIG. 3 shows an example neural network architecture for 2D transformation. Four output channels are formed by the split layers, which are input to the network for recursive calls. The network for recursive calls outputs four channels, which are input to the twiddle layer using learned phases for each input channel or for one less than the total number of channels. The four channel outputs of the twiddle layer are provided to the convolution layer forming the butterfly layer. The reconstructed output is used to form the output image.

Figure 4:
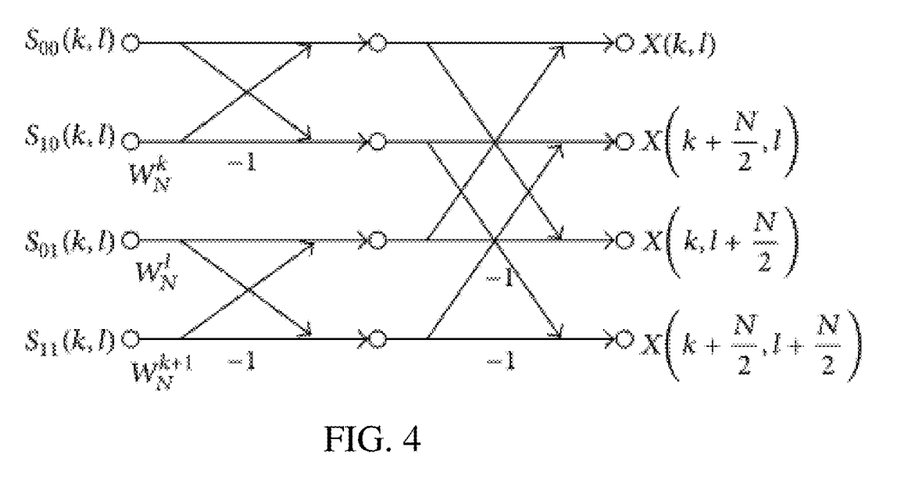
FIG. 4 illustrates an example butterfly layer.

FIG. 4 shows an example arrangement of the butterfly layer, which receives the four input channels as weighted with the twiddle weights. The arrangement reflects the matrix operation of the 1, −1 matrix. FIG. 4 shows the sum and difference operation of the butterfly operation for two dimensions—two channels for the two dimensions with each channel having odd and even inputs. The butterfly layer is implemented with a convolution layer without enforcing the matrix.

The network architecture maintains the complexity of O(N log N) where O is the number of parameters and N is the amount of input data. The overall complexity remains in O(N log N) as long as the split layer does not expand the total data size. The network architecture (RadixNet) may be extended to multidimensional operators by splitting the input along all dimensions simultaneously (e.g. (2, 2) stride and 4 output channels in 2D). The deep network architecture is based on the radix FFT to learn optimal reconstruction operators that remain in the same O(n log n) complexity class as the FFT. The depth and width of the CNN used in the architectures are design parameters, but the number of output channels of the split network is maintained at 2 per dimension to preserve the complexity.

A machine (e.g., reconstruction processor, workstation, computer, or server) performs machine training using the network architecture. The network is trained to transform based on having learned from the training data (e.g., input sample sets, the ground truth outputs, and any other information). End-to-end training is used for the radix network and/or for the reconstruction network including the radix network. End-to-end training is performed, but one or more features may be set. Machine learning is performed to train the various units using the defined architecture. The features (e.g., convolution kernels, weights, phases, connections, and/or other parameters) that are determinative or map to the ground truth are learned. The features providing the desired transform are learned.

For training, a L2-norm loss is used to optimize the network. Other error functions may be used. In one embodiment, the weights of the network are randomly initialized. Another initialization may be used, such as initializing with FFT coefficients. The optimization is with the Adam optimizer, but other optimization functions (e.g., RMSprop, SGD, etc.) may be used. During the optimization, the different distinguishing features are learned.

For compressed sensing MR, the training of the network is initialized. The network is initialized with nonlinearities able to perform FFT, such as Cooley-Tukey coefficients. The learning starts with the defined network architecture and these initialized parameters. The FFT is substituted by ReLUs for positive and negative inputs. The split is for positive and negative, so the split layer forms four channels—positive even, positive odd, negative even, and negative odd. For example, the split layer includes three convolution layers—first convolution layer with 1 input channel, 2 output channels, kernel size 2 and stride 2; second convolution layer with 2 input channels, 4 output channels, kernel size 3, stride 1, padding 0, and groups 2; and third convolution layer with 4 input channels, 2 output channels, kernel 3, stride 1, padding 0, and groups 2. A ReLU layer is provided between the second and third convolution layers. Another example repeats the second, ReLU, and third layers multiple times. The butterfly layer or other layer combines the positive and negative.

The training may be on-going, such as periodically updated. For example, online or other updated learning is performed. As new samples are acquired, the learning is repeated in total or to incorporate the further training data.

Once trained, the machine-learned neural network performs the transform in act 14 given input scan data for a patient. For example, k-space data measured from a patient is input by a reconstruction processor to the machine-learned neural network. The machine-learned neural network outputs data in the image or object domain for that patient based on the k-space data. The reconstruction processor applies the machine-learned network instead of a FFT function. A further part of the network, other network, or hand-coded process uses the transformed data as part of reconstruction in act 12. The machine-learned network may be trained to provide an inverse transform. Multiple machine-learned networks may be used to transform and inverse transform as part of an iterative reconstruction.

In act 16, a display screen displays an image of the patient. The image is generated from the object or image domain data. After transformation and reconstruction, the data representing a plane or volume of the patient is provided. Image processing is applied to generate a display image. For example, 3D rendering is performed to generate a 2D image from a given perspective. Mapping, scaling, cropping, segmentation, filtering, and/or another image processing may be applied.

In one embodiment, a MR image is displayed. The image domain data transformed by the network from k-space data is used to generate an MR image. The MR image is displayed as a 2D MR image, either representing a plane or as rendered from a volume. The image may be scalar values per pixel or voxel location or may be mapped to RGB values for display.

Figure 5:
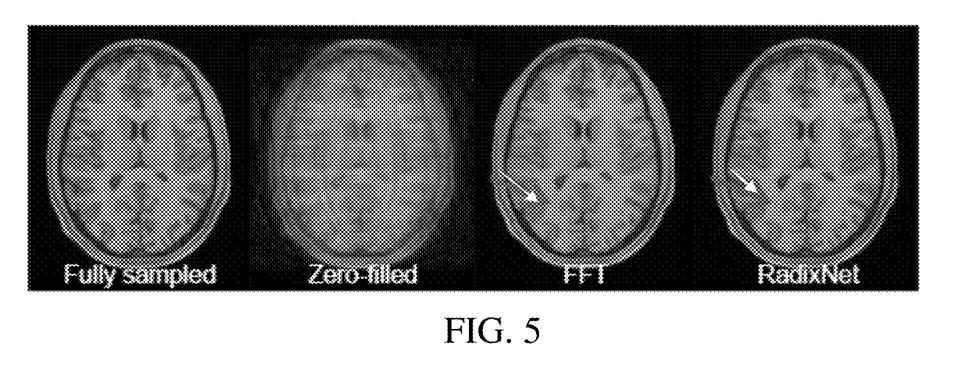
FIG. 5 shows four images reconstructed using different approaches.

FIG. 5 shows an MR image generated from k-space data using the RadixNet (i.e., using the architecture of FIG. 2 for transformation). Two networks are trained to reconstruct 2D axial T1w brain images from the Human Connectome Project. 900 subjects are used with an 850 training/50 validation split and 64 slices per subject for a total of 57600 images of fixed dimensions 256×256. A fixed variable density sampling pattern with 5× acceleration and front-to-back readout direction is used to generate the input k-space data. Two iterative proximal gradient networks with a U-net regularization are trained to reconstruct the images. One network is trained with 2D forward and adjoint FFTs as operators in the gradient computation. The other network is trained with shallow (split, twiddle, and butterfly blocks are each composed of a single layer) linear 2D-RadixNets initialized with the Cooley-Tukey coefficients. The weights of the U-net are initialized to i.i.d. Gaussian values with 0 mean and standard deviation 1e-3. Training uses an $L_2$ loss and the Adam algorithm with mini-batch size 16 and learning rate 1e-4.

After training, the RadixNet based FFT outperformed the FFT by 1.2 dB in validation PSNR (36.6 dB vs 35.4 dB). FIG. 5 shows a validation example with the ground truth (i.e., fully sampled), zero-filled image, and network outputs (FFT and RadixNet). These empirical results show that fast transform networks may be trained at 256×256 dimensions and outperform the FFT. Greater resolution and/or 3D application may be provided using the RadixNet. Deeper (e.g., greater number of layers) RadixNet may enable the reconstruction to correct for forward imaging model imperfections such as trajectory errors or patient motion. Parallel imaging may be provided.

FIG. 6 shows a medical imaging system for reconstruction in medical imaging. A neural network is machine trained and/or applied to receive scan data as input and output a transformation of the scan data in an image or object domain. To provide for greater resolution, the complexity is minimized by using a network architecture modeled after the radix FFT or Cooley-Tukey FFT. The architecture includes a split of data into two or more paths with the transform being applied by recursive call separately for each path.

The medical imaging system includes the display 64, memory 68, and reconstruction processor 66. The display 64, reconstruction processor 66, and memory 68 may be part of the MR scanner 62, a computer, server, or other system for image processing medical images from a scan of a patient. A workstation or computer without the MR scanner 62 may be used as the medical imaging system. Additional, different, or fewer components may be provided, such as including a computer network for remote image generation of locally captured scans or for local image generation from remotely captured scans. The machine-learned neural network is applied as a standalone application on the workstation or a local device or as a service deployed on network (cloud) architecture.

The medical imaging system is for training, such as using measurement domain data (e.g., k-space data) and ground truth image domain data from the memory 68 and/or MR scanner 62 as input. Alternatively, the medical imaging system is for application of the machine-learned network as trained.

The MR scanner 62 is a medical diagnostic imaging system configured to scan a volume of a patient and generate anatomical information from the scan. In one embodiment for application of the machine-learned network, a main magnet or coil generates a substantially uniform magnetic field through the patient 60. Gradient coils, local coils, and/or a whole-body coil generate a pulse sequence to shift spin axes of molecules in the patient away from the uniform magnetic field lines. The local coils and/or whole-body coil detect radio frequency emissions caused by the relaxation of the spin axes of the molecules returning to the magnetic field lines. This k-space data is reconstructed into an object or spatial domain. After transform, the scan or image data represents tissue response from a region of the patient 60. The pulse sequence may be repeated or continues to obtain scan data representing the region over time. Any MR imaging pulse sequence or scanning may be used. Other medical scanners may be used, such as CT, ultrasound, PET, or SPECT.

The reconstruction processor 66 is a control processor, general processor, digital signal processor, three-dimensional data processor, graphics processing unit, application specific integrated circuit, field programmable gate array, digital circuit, analog circuit, artificial intelligence processor, combinations thereof, or other now known or later developed device for reconstruction, transformation, and/or application of a machine-trained neural network. The reconstruction processor 66 is a single device, a plurality of devices, or a network. For more than one device, parallel or sequential division of processing may be used. Different devices making up the reconstruction processor 66 may perform different functions. In one embodiment, the reconstruction processor 66 is a control processor or other processor of a medical diagnostic imaging system, such as the MR scanner 62. The reconstruction processor 66 operates pursuant to stored instructions, hardware, and/or firmware to perform various acts described herein, such as controlling scanning, transforming scan data, reconstructing an image, and/or generating an output image.

The reconstruction processor 66 is configured to train a machine learning architecture. Based on a user provided or other source of the network architecture and training data, the reconstruction processor 66 learns features to train the network to transform and/or reconstruct. The result of the training is a machine-learned network for generating image domain data or a reconstructed image (e.g., MR image) from input scan data (e.g., k-space data) for a patient.

Alternatively or additionally, the reconstruction processor 66 is configured to apply one or more machine-learned networks. An image-to-image or U-net neural network is applied to reconstruct an image from the scan data. A machine-learned neural network having a radix FFT architecture transforms as part of the reconstruction or as a separate call from reconstruction. The reconstruction may be the transformation by application of the network with the split layer and following recursive call layers. Hand-coded reconstruction from the transformed data may be implemented by the reconstruction processor 66. Use of the radix FFT-based architecture allows for transformation of data for a greater resolution and more efficient computation than a fully connected network.

In one embodiment, the reconstruction processor 66 is configured to perform forward or adjoint measurement operations as part of iterative reconstruction. The forward and/or adjoint measurement operations transform between the measurement and image domains. At least one of the forward or adjoint operations use application of a machine-learned neural network. For example, two machine-learned neural networks are used, one for forward and another for adjoint. The machine-learned neural network for transformation includes a convolutional splitting layer with a stride of 2 or greater, parallel recursive deep networks, a diagonal linear layer, and a convolutional butterfly layer.

The reconstruction processor 66 may be configured to output a spatial distribution of the tissue or patient. This output may be used to render an image to a display. In other embodiments, the spatial distribution is used to calculate a value for a quantification. The value is output in an image.

The display 64 is a CRT, LCD, projector, plasma, printer, tablet, smart phone or other now known or later developed display device for displaying the output, such as the MR image reconstructed from k-space data. The display 64 displays a medical image for diagnosis, prognosis, and/or treatment.

The instructions, training data, network definition, features, machine-learned network, outputs, and/or other information are stored in a non-transitory computer readable memory, such as the memory 68. The memory 68 is an external storage device, RAM, ROM, database, and/or a local memory (e.g., solid state drive or hard drive). The same or different non-transitory computer readable media may be used for the instructions and other data. The memory 68 may be implemented using a database management system (DBMS) and residing on a memory, such as a hard disk, RAM, or removable media. Alternatively, the memory 68 is internal to the processor 76 (e.g. cache).

The instructions for implementing the training or application processes, methods, and/or techniques discussed herein by a processor are provided on non-transitory computer-readable storage media or memories, such as a cache, buffer, RAM, removable media, hard drive or other computer readable storage media (e.g., the memory 68). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for converting data between scan space and image domain in an imaging system, the method comprising:
    scanning, by the imaging system, an object, the scanning resulting in input data representing the patient;
    performing a fast transform of the input data based on application of the input data to a machine-learned neural network, the machine-learned neural network comprising an architecture of a sequence of a convolutional splitting layer, parallel recursive deep networks, a diagonal linear layer, and a convolutional butterfly layer;
    generating image domain data from an output of the machine-learned neural network; and
    displaying an image from the image domain data,
    wherein performing comprises performing with the recursive deep networks comprising nested radix fast Fourier transform networks at iteratively reducing scales.

2. The method of claim 1 wherein performing comprises performing with the architecture of the machine-learned network being structured as a radix fast Fourier transform.

3. The method of claim 1 wherein performing comprises performing with the convolutional spitting layer have a stride of R, R being two or greater.

4. The method of claim 1 wherein performing comprises performing with the nested radix fast Fourier transform networks having unshared weights.

5. The method of claim 4 wherein performing comprises performing with a number of output channels being equal to a number of a stride of the convolution splitting layer.

6. The method of claim 5 wherein performing comprises performing with the convolution splitting layer being two-dimensional, the number of output channels being four and the stride being four.

7. The method of claim 5 wherein performing comprises performing with a complexity of O(N log N) where N is a total number of samples of the image domain data.

8. The method of claim 1 wherein performing comprises performing with the diagonal layer being a twiddle layer.

9. The method of claim 8 wherein the twiddle layer comprises a neural network layer defined to learn weights in diagonal linear operations.

10. The method of claim 1 wherein performing comprises performing with the convolution butterfly layer being a sum and difference-based convolutional layer.

11. The method of claim 1 wherein generating the image domain data comprises reconstructing with a machine-learned reconstruction network trained with gradient descent and regularization and including the machine-learned neural network.

12. The method of claim 1 wherein displaying comprises displaying the magnetic resonance image as a two-dimensional magnetic resonance image.

13. A system for reconstruction in medical imaging, the system comprising:
    a medical scanner configured to scan a patient, the scan providing scan data;
    a reconstruction processor configured to perform a fast transform of the scan data based on application of the scan data to a machine-learned neural network, the machine-learned neural network comprising an architecture of a sequence of a convolutional splitting layer, parallel recursive deep networks, a diagonal linear layer, and a convolutional butterfly layer and configured to generate image domain data from an output of the machine-learned neural network; and
    a display configured to display the image domain data as reconstructed from the scan data,
    wherein perform comprises performing with the recursive deep networks comprising nested radix fast Fourier transform networks at iteratively reducing scales.

14. The system of claim 13 wherein the medical scanner comprises a magnetic resonance scanner and where in the image comprises a magnetic resonance image.

15. The system of claim 13 wherein the machine-learned neural network comprises blocks having a radix fast Fourier transform architecture.

16. The system of claim 13 wherein the machine-learned neural network is configured to perform forward or adjoint measurement operations.

17. A method for Fourier transform-based reconstruction in a medical imaging system, the method comprising:
    scanning, by the medical imaging system, a patient, the scanning resulting in scan data representing the patient;
    reconstructing an image of the patient from the scan data, the reconstructing including performing a fast transform of the scan data based on application of the scan data to a machine-learned neural network, the machine-learned neural network comprising an architecture of a sequence of a convolutional splitting layer, parallel recursive deep networks, a diagonal linear layer, and a convolutional butterfly layer;
    generating the scanned image of the patient from an output of the machine-learned neural network; and
    displaying the image of the patient,
    wherein performing comprises performing with the recursive deep networks comprising nested radix fast Fourier transform networks at iteratively reducing scales.

18. The method of claim 17 wherein reconstructing comprises reconstructing with the transformation being a fast Fourier transformation and the trained neural network including the layer with a diagonal operator after the layer for recursive calls and the convolution butterfly layer after the layer with the diagonal operator.

19. The method of claim 17 wherein reconstructing further comprises reconstructing with the trained neural network having an architecture with a Cooley-Tukey fast Fourier transform structure, the structure including the convolution layer to split and the layer for the recursive calls.

* * * * *